United States Patent [19]

Duff et al.

[11] Patent Number: 5,064,530

[45] Date of Patent: Nov. 12, 1991

[54] FLUID CONTAMINATION DETECTING APPARATUS

[75] Inventors: David A. Duff, P.O. Box 246, Chavies, Ky. 51727; Daniel S. Gove, Franklin, Tenn.; Edward E. Schmillen, Metamora, Ill.

[73] Assignees: Caterpillar Inc., Peoria, Ill.; David A. Duff, Chavies, Ky.

[21] Appl. No.: 533,208

[22] Filed: Jun. 4, 1990

[51] Int. Cl.$^5$ ............................................. B01D 35/06
[52] U.S. Cl. .................................... 210/94; 210/222;
  210/223; 210/512.1; 210/512.3; 210/93;
  210/95; 210/168; 73/53; 73/611 R
[58] Field of Search ............... 210/222, 223, 512.1,
  210/512.3, 415, 90, 93, 94, 95, 168; 324/700;
  73/53, 61.1 R

[56] References Cited

U.S. PATENT DOCUMENTS

| | | | |
|---|---|---|---|
| 3,356,216 | 5/1967 | Sato | 210/94 |
| 3,681,562 | 9/1972 | Winzen | 210/94 |
| 3,827,558 | 8/1974 | Firth | 210/90 |
| 3,992,296 | 11/1976 | Nobuta | 210/90 |
| 4,333,826 | 6/1982 | Albertson | 210/94 |
| 4,823,625 | 4/1989 | Hamilton | 324/700 |
| 4,834,464 | 5/1989 | Frehse | 210/222 |

Primary Examiner—Robert A. Dawson
Assistant Examiner—David Reifsnyder
Attorney, Agent, or Firm—William C. Perry

[57] ABSTRACT

Fluid reservoirs are often provided with a means by which the severity of fluid contamination may be monitored. One method of checking the condition of the fluid, requires the disassembly or removal of one or more components from the associated reservoir in order to read the monitoring device. Another method is utilized in conjunction with the filtration system of the fluid and an indication is observed when the level of contamination reaches a predetermined point. The present invention provides an apparatus whereby the condition of a fluid may be continually observed without requiring the disassembly or removal of any components attached to the fluid reservoir, regardless of the condition of the fluid.

18 Claims, 2 Drawing Sheets

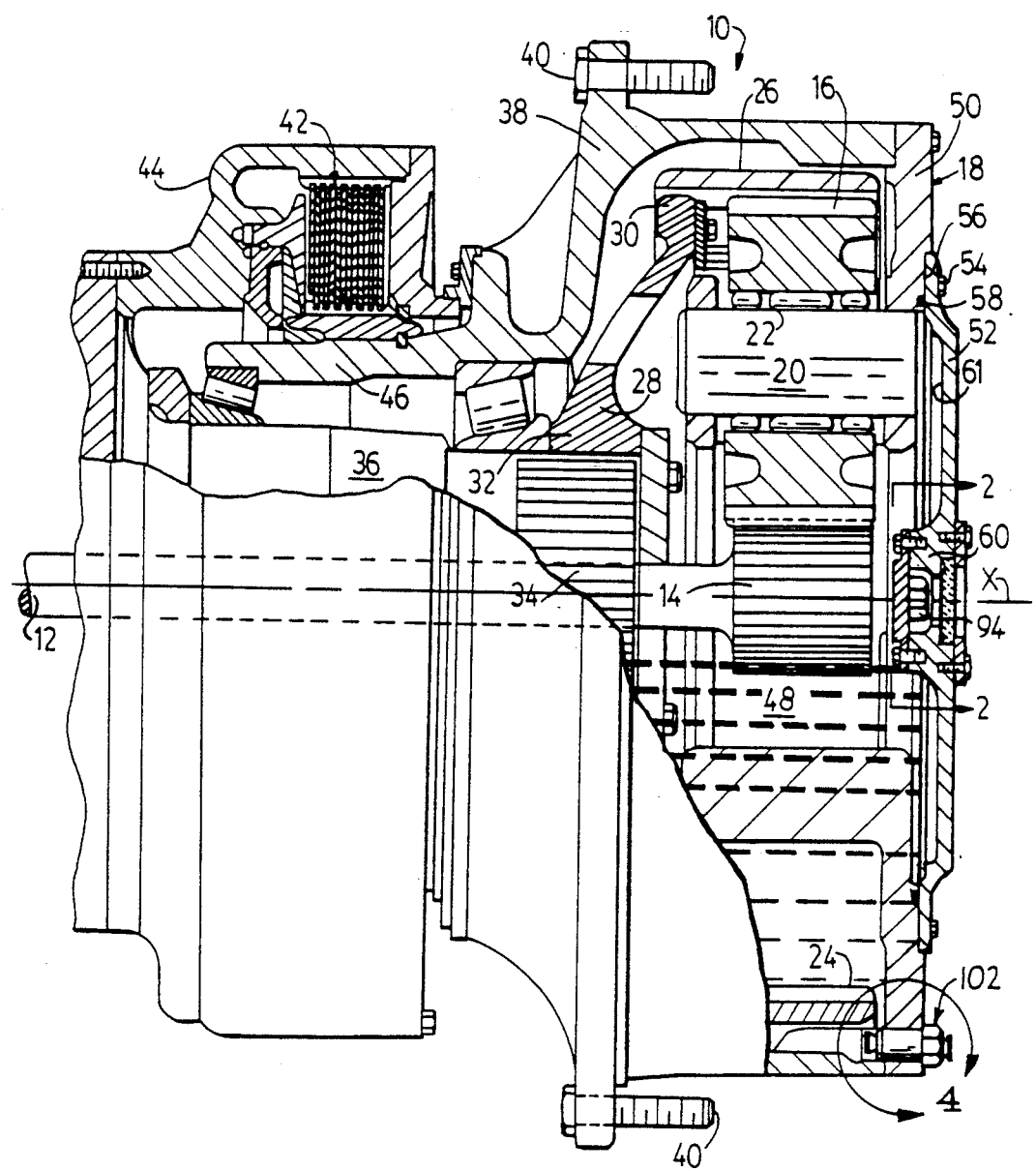
Fig_1

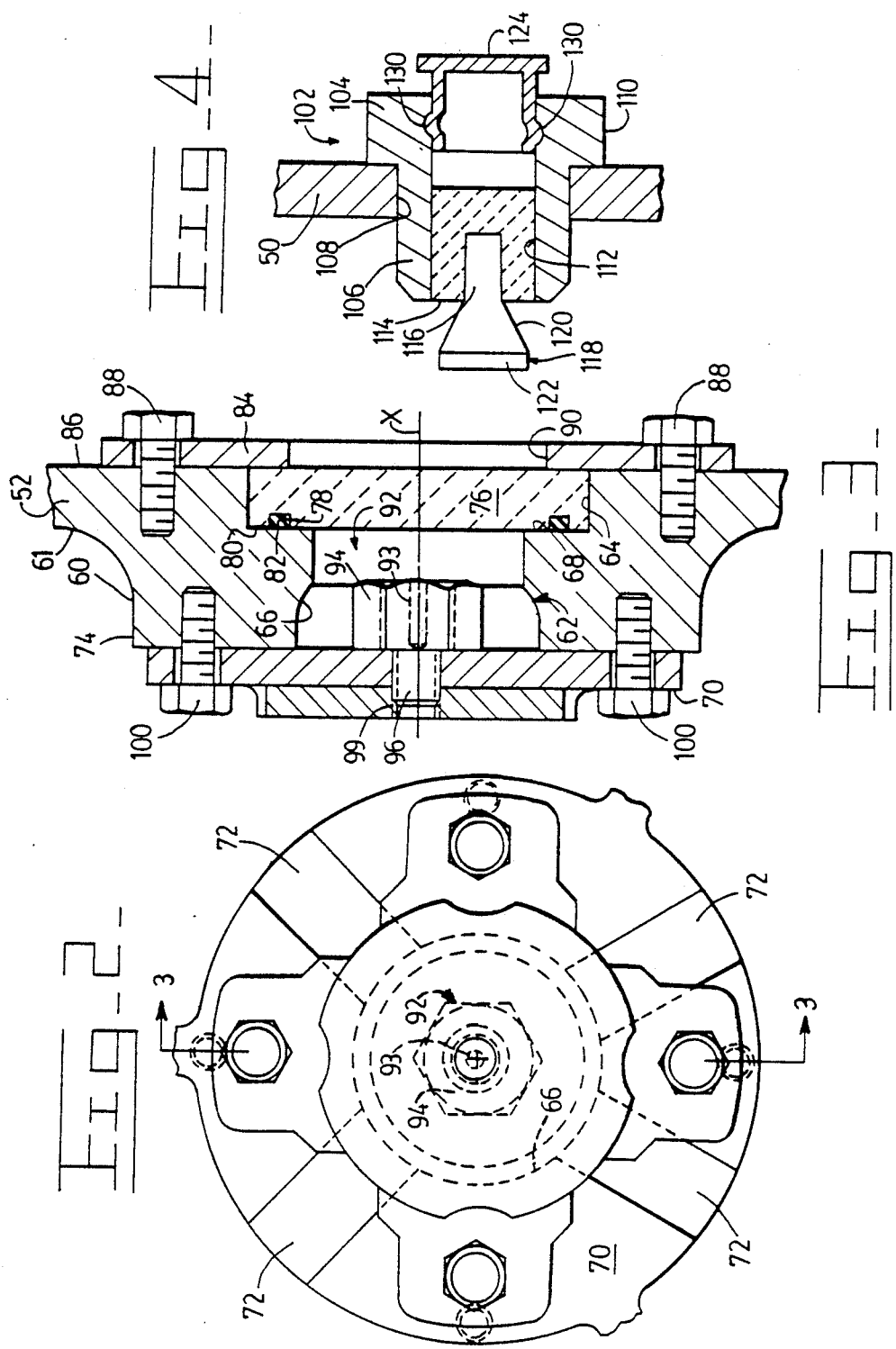

FLUID CONTAMINATION DETECTING APPARATUS

DESCRIPTION

1. Technical Field

This invention relates generally to an apparatus for detecting the contamination of fluid and more particularly to an apparatus that will detect and visually indicate the contamination of oil within a reservoir.

2. Background Art

In the past, there have been several different ways developed to detect the contamination of fluid within a closed circuit. It is most common, however, to tie the detecting device to the operation of the filter mechanism. As the filter becomes clogged with the increased contamination of the fluid, the pressure of the fluid passing through the filter also increases. Most contamination detecting devices utilize this increase in pressure as a basis for their operation. It is common to provide a filter assembly with a by-pass system to allow passage of fluid through the filter housing even though the filter element is clogged. One such device is disclosed in U.S. Pat. No. 3,827,558 issued on Aug. 6, 1974, to Robert L. Firth. A filter assembly is shown to have a housing in which two windows are mounted. On the inner side of each window is positioned an indicating tab that is secured at a lower end to a bypass member. When the filter assembly becomes clogged, the bypass member is shifted to allow the fluid to pass around the filter element. As the bypass member shifts, so too does the indicating member. This movement is visible when viewed through the windows. The major drawback resides in the isolation of the indicating means from the fluid itself. There is no way to determine whether the contamination is a result of normal operation or from particles that have entered the fluid as a result of a component failure. It is not the fluid itself that is being observed but rather, the condition of the filter.

Another device for indicating the contamination of a filter is disclosed in U.S. Pat. No. 3,992,296 issued to Kouji Nobuta on Nov. 16, 1976. This particular device utilizes a transparent dome-like structure to house a bellows that, under normal conditions, has an upper portion that is positioned immediately adjacent the inner face of the dome. The lower portion of the bellows is spaced from the inner face of the dome and captures a small amount of fluid therebetween. A plunger that is attached on one end to the inner face of the upper portion of the bellows, is attached at its opposite end to a bypass mechanism within the filter assembly. When a bypass condition is achieved, the piston will shift, and with it the bellows, in a direction away from contact with the inner surface of the dome. As this occurs, the fluid trapped at the lower portion of the bellows fills the void created by the movement of the upper portion of the bellows. This creates a visible difference in the appearance of the dome to indicate the by-pass condition of the filter. This patent suffers the same drawbacks set forth above. The actual condition of the operating fluid is not visible and the exact cause of the contamination cannot be readily determined.

The subject invention provides an apparatus that provides a continuous visual indication of the condition of the operating fluid. When utilized in conjunction with a vehicle system wherein several rotating components operate in a continual bath or circuit of oil, the apparatus will collect any particles that may be suspended in the oil to indicate accurately how badly the oil is contaminated. Any catastrophic failure of one of the components is often preceded by the gradual break-up of one or more components. This break-up would be readily observable and corrective action could be taken before any further damage to surrounding components occurs.

The present invention is directed to overcoming one or more of the problems set forth above.

DISCLOSURE OF THE INVENTION

In one aspect of the present invention an apparatus for detecting the contamination of a quantity of fluid maintained within a reservoir is provided. It includes a means for sealably covering one end of the reservoir that defines an opening formed therethrough. A transparent member is placed in overlying relation to the opening in the cover member and is sealingly engaged with the cover. A means for collecting impurities suspended within the fluid is provided and is positioned adjacent the inner side of the transparent member in a manner wherein the collected impurities are visible when viewed from the opposite side of the transparent member.

With a contamination detecting apparatus as described above, a visual indication of the condition of the fluid is continually provided. When utilized in conjunction with a mechanical drive system, the condition of the operating fluid, such as lubricating oil may be monitored on a regular basis to gauge the condition of the components. In the event that one of the mechanical components is about to fail, several ferrous particles would appear on the magnets of the impurity collecting means. In such instances, corrective action could be taken before a catastrophic failure of the entire drive occurred.

BRIEF DESCRIPTION OF THE DRAWINGS

FIG. 1 is a diagrammatic cross-sectional view of a vehicular final drive that embodies the principles of the present invention;

FIG. 2 is an enlarged fragmentary end view, taken along lines 2—2 as shown in FIG. 1; and FIG. 3 is an enlarged sectional view taken along lines 3—3 of FIG. 2.

FIG. 4 is an enlarged sectional view taken along circular line 4 of FIG. 1.

BEST MODE FOR CARRYING OUT THE INVENTION

Referring now to FIG. 1, a final drive mechanism for providing rotation to the wheels of a vehicle is shown generally at 10. Drive from an input shaft 12 is provided by a sun gear 14 that is engaged with a plurality of planet gears 16 (one shown). The planet gears 16 are mounted to a planet carrier 18 via mounting pins 20. A bearing 22 is positioned between the planet gears 16 and the pins 20 to allow relative rotation therebetween. The planet gears are in turn engaged with the internal splines 24 of a ring gear 26. The ring gear is supported by a hub member 28 that is engaged at its outer end 30 with the splines 24 of the ring gear 26 and is mounted on its inner end 32 to a splined portion 34 of a non-rotating wheel spindle 36. As the sun gear 14 rotates, the planet gears 16 are caused to rotate within ring gear 26. Rotation of the planet gears 16 within the ring gear 26 causes the movement of the mounting pins 20 about the input shaft 12 and thus the rotation of the carrier 18. The carrier forms a portion of a wheel hub 38 to which a wheel and tire assembly (not shown) are attached by way of a plurality of studs 40.

Inboard of the final drive mechanism 10 is a brake assembly 42 that is positioned between a stationary housing 44 and an inward extension 46 of the wheel hub 38 to selectively prevent rotation of the wheel in a conventional manner. The stationary housing 44, the attached wheel hub 38, and the planet carrier 18 form an enclosure that serves as a reservoir 48 for lubricating fluid, such as oil, to lubricate the drive components as they rotate in response to rotational input from the shaft 12.

On an outboard wall 50 of the carrier 18 a centrally disposed cover member or plate 52 is attached by any suitable fastener such as bolts 54. The cover 52 engages an outer face 56 of the carrier 18 and a seal 58 is provided therebetween to prevent leakage of the fluid from within the reservoir 48. An inwardly extending boss 60, which is best shown in FIGS. 2 and 3 is formed on an inwardly facing wall 61 of cover 52 and is disposed about the horizontal centerline X thereof. An opening 62 in the form of a stepped bore is defined through the boss 60. The stepped bore 62 comprises first and second portions 64 and 66, respectively, that are joined by a vertical wall 68. The innermost portion of the boss 60 terminates at a vertically extending face 70. A plurality of radially extending passages 72 are defined in the vertical face 70 and extend between the second portion 66 of the stepped bore 62 to an outer periphery 74 of the boss 60.

A transparent member or sight glass 76 is provided that is of sufficient diameter to be received within the first portion 64 of the stepped bore 62. A groove 78 is defined on an inwardly facing surface 80 of the sight glass and is adapted for receiving a seal member 82 such as an O-ring seal. The seal engages the vertically extending end wall 68 that is defined by the stepped bore 62. The sight glass 76 is held in sealing engagement within the stepped bore 62 by a secondary cover plate 84 to prevent leakage of fluid from within the reservoir. The secondary cover plate 84 is attached to the outer surface 86 of the primary cover plate 52 by any suitable readily removable fasteners, such as bolts 88. The secondary cover plate 84 defines an aperture 90, through which the sight glass 76 may be observed.

The sight glass 76 may be comprised of glass, Plexiglas, polycarbonate or any other suitable transparent material. As a secondary option, the material may be ground to provide the sight glass with a certain degree of magnification.

A means 92 for collecting impurities suspended in the oil is positioned within the second portion 66 of the stepped bore 62 in a manner wherein it will be immersed, or generally exposed to, at least a partial flow of the fluid. In the illustrated embodiment, the impurity collecting means includes a magnetic member 93 that is secured to a mounting plate 98 by any suitable means. In the subject invention, the magnetic member 93 is bonded to and encased within a hexagonally shaped, non-magnetic housing 94 that is provided with a stud 96 that is threadably received within an aperture 99 formed in the mounting plate 98. The mounting plate is in turn secured as by bolts 100 or other suitable fastener, to the vertical face 70 of the boss 60. When the mounting plate 98 is secured to the boss 60 the magnetic member 93 is positioned immediately adjacent the sight glass 76. Being so positioned, any ferrous particles adhering to the magnetic member may be readily seen from the area outside the secondary cover plate 84 without having to remove or disassemble any structure.

While the present invention is illustrated for use with a boss that is centrally positioned on the cover plate, it is to be understood that the boss and thus the impurity collecting apparatus may be offset from the centerline. In being so positioned, the passages 72 could be eliminated since the eccentric movement of the collecting means through the oil would be sufficient to obtain an accurate reading of oil contamination.

Referring now to FIGS. 1 and 4, the impurity collecting means 92 is alternatively illustrated in conjunction with a means 102 by which the fluid in the reservoir may be drained. The drain plug 102 is shown in FIG. 1 at the lower extremity of the cover plate 50 in a position sufficient for draining the reservoir 48. The drain plug comprises an outer body 104 that has a threaded portion 106 that is engaged with a threaded bore 108 in the outer wall 50 of the carrier 18. An outer end portion 110 of the outer body 104 is formed in the shape of a hexagon to facilitate engagement with a socket wrench or the like. A through bore 112 extends the entire length of the outer body 104 and receives a transparent member or sight glass 114 in the inner, or leftmost, end portion of the bore 112 as viewed in FIG. 4. The sight glass 114 is fixed within the through bore 112 as by bonding or similar process. A magnetic member 116 extends inwardly from the sight glass 114 to position an enlarged end portion 118 thereof in spaced relation to the sight glass 114 to provide a magnetic surface 120 that is exposed to the fluid housed within the reservoir. In the illustrated embodiment, the magnetic surface 120 is generally frusto-conical in configuration to provide a relatively large surface area on which ferrous particles may become attached. While this surface is illustrated as being frusto-conical, it is to be understood that it may take the form of any one of various configurations without departing from the scope of the subject invention. A non-magnetic cover member 122 is positioned about the enlarged end portion 118 of the magnetic member 116 in a manner to encapsulate the magnetic member on all sides except those facing the sight glass 114. To increase the visibility of the impurities collected on the magnet, it may be desirable to utilize a non-magnetic material that is highly reflective to encapsulate the magnetic member. In doing so, the reflective material could be used in conjunction with a beam of light from a source such as a flashlight or fiber optics that would be directed through the sight glass 114 from the opposite, or external side of the drain plug 102. A dust cover 124 made of plastic or other deformable material is provided that is generally cup-shaped in configuration and defines a tubular extension 126. An outwardly extending ridge 128 is defined about one end portion thereof and is sufficient for nesting engagement with a circumferential groove 130 that is defined in the through bore 112 of the outer body 104. When positioned as such, the dust cover is held from being inadvertently dislodged by vehicle vibration or other unintentional means while protecting the transparent member 114 from undue exposure to the elements.

INDUSTRIAL APPLICABILITY

When the final drive mechanism 10 is in operation, the entire outer structure including the carrier 18 and the wheel hub 38 are rotated to provide drive to the wheels. As this rotation occurs, the internal components are continually being immersed in the quantity of oil maintained within the housing which serves as a reservoir 48. As the components wear, tiny particles of ferrous material become suspended in the oil. As the cover plate 52 is rotated through the oil, some residual oil remains on the inner surface 61 of the cover member 52. As the oil runs down the surface 61, the passages 72 pick up a certain amount of the oil and direct it past the magnetic member 93. When any of the impurities suspended in the oil are directed towards the magnetic member, they will become captured in an area that is readily visible from the opposite side of the sight glass 76.

In the event that one of the components in the final drive mechanism 10 becomes excessively worn out and/or is about to fail, the amount of particles suspended in the oil will increase substantially. Likewise, the amount of particles trapped by the magnetic member 93 will increase substantially. This increase will be readily visible to the operating or service personnel as they make their daily inspection. The sight glass 76 may be removed to provide access to the magnets 94 and 9 and the particles for removal and further analysis. It is at this point that a determination may be made to tear down the final drive and repair any worn or damaged parts before a catastrophic failure of the entire final drive occurs.

In the instance that the impurity collecting apparatus is used in conjunction with a drain plug 102, the dust cover 124 may be removed to view the sight glass 114. Since the tubular extension 126 is made of deformable material, an outwardly directed force will cause the ridge 128 to dislodge from its engagement with the circumferential groove 130, thus allowing removal of the dust cover from the through bore 112. Upon removal of the dust cover, visual access to the sight glass 114 is afforded. Since the sight glass is somewhat recessed within the outer body 104 of the drain plug 102, it may be desirable to use a flashlight or other available light source to illuminate the area. In the event that a non-magnetic, reflective material is utilized to encase the magnetic surface, the light from the flashlight will be reflected back through the sight glass 114 to effectively "backlight" the particles attached to the magnetic surface. If after inspection, removal of the drain plug 102 is required, the vehicle must be moved to position the drain plug above the level of the fluid within the reservoir (if not already so positioned). The drain plug may then be removed for closer inspection and cleaning without loss of fluid from the reservoir.

Other aspects, objects and advantages of this invention can be obtained from a study of the drawings, the disclosure and the appended claims.

We claim:

1. An apparatus for detecting the contamination of a quantity of fluid, comprising
    a drive mechanism defining a reservoir;
    means for covering one end portion of the reservoir, said covering means having an opening formed therethrough and being positioned for sealing engagement with the reservoir;
    a transparent member positioned within the opening in the covering means and being sealingly engaged therewith; and
    means for collecting impurities suspended within the fluid, said means being positioned adjacent an inner side of the transparent member in a manner such that said collected impurities are visible when viewed from a point outside the transparent member.

2. The apparatus as set forth in claim 1 wherein the drive mechanism further includes:
    a stationary housing;
    a wheel hub;
    a planet carrier sealingly mounted to the wheel hub; and
    a cover plate sealingly mounted to the planet carrier.

3. The apparatus as set forth in claim 1 wherein the means for covering the reservoir includes a vertically oriented end plate.

4. The apparatus as set forth in claim 1 wherein the impurity collecting means is disposed about a centerline defined by the covering means.

5. The apparatus as set forth in claim 1 wherein the impurity collecting means is offset from the centerline of the covering means and is immersible in fluid contained within the reservoir.

6. The apparatus as set forth in claim 1 wherein the covering means further defines an inwardly disposed boss about a centerline of the opening.

7. The apparatus as set forth in claim 6 wherein the opening in the covering means further includes a stepped bore having a first portion having a diameter sufficient for receiving and mounting the transparent member and a second portion having diameter sufficient for receiving the impurity collecting means therein.

8. The apparatus as set forth in claim 7 wherein a plurality of fluid passages extend from the second portion of the opening to an outer periphery of the boss to allow fluid in the reservoir to pass through the boss, said fluid being directed past the magnetic member as it flows therethrough.

9. The apparatus as set forth in claim 1 wherein said impurity collecting means further includes a magnetic member that is positioned in the opening in inwardly adjacent relation to the transparent member, said magnetic member being secured to a mounting plate.

10. The apparatus as set forth in claim 9 wherein the magnetic member further includes a magnet that is encased in a hexagonally shaped non-magnetic housing and is secured to the mounting plate by a threaded stud that extends from the housing. through the boss, said fluid being directed past the magnetic member as it flows therethrough.

11. The apparatus as set forth in claim 1 wherein the impurity collecting means is incorporated into a drain plug assembly positioned within a bore in the covering means, said plug assembly being positionable with respect to the reservoir to allow the fluid to be drained therefrom.

12. The apparatus as set forth in claim 11 wherein the drain plug assembly further includes:
    an outer body portion having a bore extending therethrough;
    a transparent member positioned within an inner end portion of the bore;
    a magnetic member extending from said transparent member to define a magnetic surface spaced from and adjacent to said transparent member.

13. An apparatus for detecting the contamination of a quantity of fluid, comprising:
    a reservoir having a predetermined quantity of fluid held therein;
    a cover member mounted on the reservoir, said cover member having a boss positioned on an inwardly facing wall, said boss defining a stepped bore having first and second portions;

a transparent member positioned within the first portion of the stepped bore;

a magnetic member positioned within the second portion of the stepped bore at a location that is adjacent the transparent member; and a plurality of fluid passages defined in the boss to allow fluid communication between the stepped bore and the reservoir, said fluid being directed past the magnetic member as it flows therethrough.

14. The apparatus as set forth in claim 13 wherein said reservoir 48 is a final drive mechanism of a vehicle, said final drive mechanism defining a housing and being rotatable with a plurality of driven members housed within the final drive and to cause the fluid in the reservoir to be directed through the passages in the boss past the magnet member.

15. The apparatus as set forth in claim 13 wherein the transparent member is a sight glass having an inwardly facing surface and a groove defined on said surface, said surface being engageable with an outwardly facing wall formed by a lip defined within the first portion of the stepped bore.

16. The apparatus as set forth in claim 15 wherein a seal member is positioned in the groove of the transparent member and is engageable with the outwardly facing wall defined by the first portion of the stepped bore.

17. The apparatus as set forth in claim 13 wherein the magnetic member further includes a mounting plate that is securable to an inwardly directed face of the boss, said magnetic member being secured to the mounting plate and extending therefrom in a direction toward the transparent member whereupon securement of the mounting plate to the boss positions the magnetic member in closely adjacent relation to the transparent member and said fluid passages.

18. An apparatus for detecting the contamination of a quantity of fluid maintained within a reservoir, comprising:

means for covering the reservoir, said covering means defining an opening therethrough and being positioned for sealing engagement with the reservoir;

a drain plug having a bore defined therethrough and being positioned within the opening formed in the covering means in a manner to allow the fluid to be drained from the reservoir;

a transparent member positioned within an inner portion of the bore defined in the drain plug; and a magnetic member attached to and extending from said transparent member to define a magnetic surface that is spaced from an adjacent to said transparent member.

* * * * *